(12) United States Patent
Mazzocca et al.

(10) Patent No.: US 8,785,191 B2
(45) Date of Patent: Jul. 22, 2014

(54) CONCENTRATION OF STEM CELLS OBTAINED DURING ORTHOPAEDIC SURGERIES

(75) Inventors: Augustus D. Mazzocca, West Hartford, CT (US); Mary Beth McCarthy, Kensington, CT (US)

(73) Assignee: University of Connecticut, Farmington, CT (US)

( * ) Notice: Subject to any disclaimer, the term of this patent is extended or adjusted under 35 U.S.C. 154(b) by 1045 days.

(21) Appl. No.: 12/199,743

(22) Filed: Aug. 27, 2008

(65) Prior Publication Data

US 2009/0060884 A1 Mar. 5, 2009

Related U.S. Application Data

(60) Provisional application No. 60/968,264, filed on Aug. 27, 2007.

(51) Int. Cl.
*C12N 5/0775* (2010.01)
*A01N 63/00* (2006.01)

(52) U.S. Cl.
USPC ......................................... 435/377; 424/93.7

(58) Field of Classification Search
None
See application file for complete search history.

(56) References Cited

U.S. PATENT DOCUMENTS

| 6,541,024 | B1 * | 4/2003 | Kadiyala et al. | 424/426 |
| 2006/0130852 | A1 * | 6/2006 | Smith et al. | 128/898 |
| 2007/0190023 | A1 * | 8/2007 | Battista et al. | 424/85.1 |
| 2008/0221527 | A1 * | 9/2008 | Bradley et al. | 604/187 |

OTHER PUBLICATIONS

Hernigou et al., "The use of percutaneous autologous bone marrow transplantation in nonunion and avascular necrosis of bone," The Journal of Bone and Joint Surgery, vol. 87-B, No. 7 (Jul. 2005).*

* cited by examiner

*Primary Examiner* — Cherie M Stanfield
*Assistant Examiner* — Paul D. Pyla
(74) *Attorney, Agent, or Firm* — Dickstein Shapiro LLP

(57) ABSTRACT

Methods for isolating and concentrating bone marrow stromal cells drawn from various surgical sites (for example, the proximal humeral head during rotator cuff repair, or the distal femur during ACL surgery) during arthroscopic or open orthopaedic surgery. The pluripotent cells obtained from the bone marrow aspirate can then be reimplanted during the same surgery to improve healing.

2 Claims, 12 Drawing Sheets

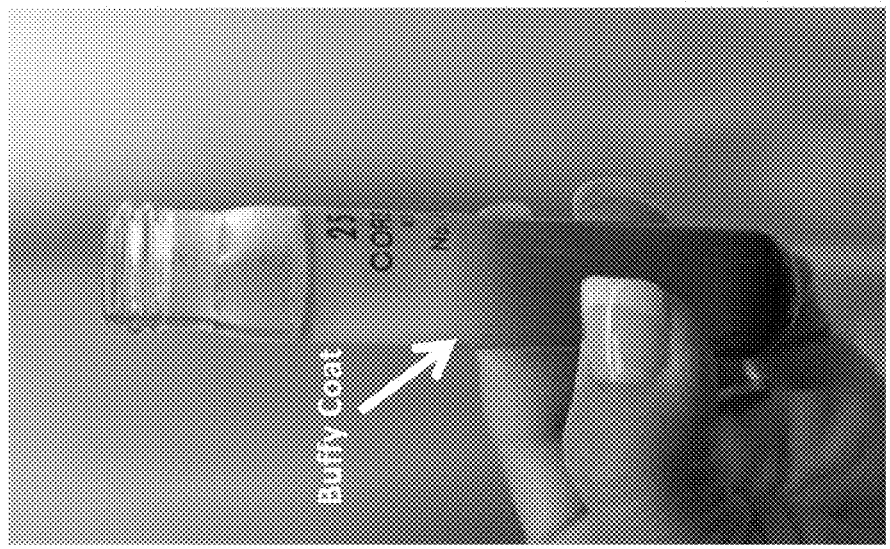

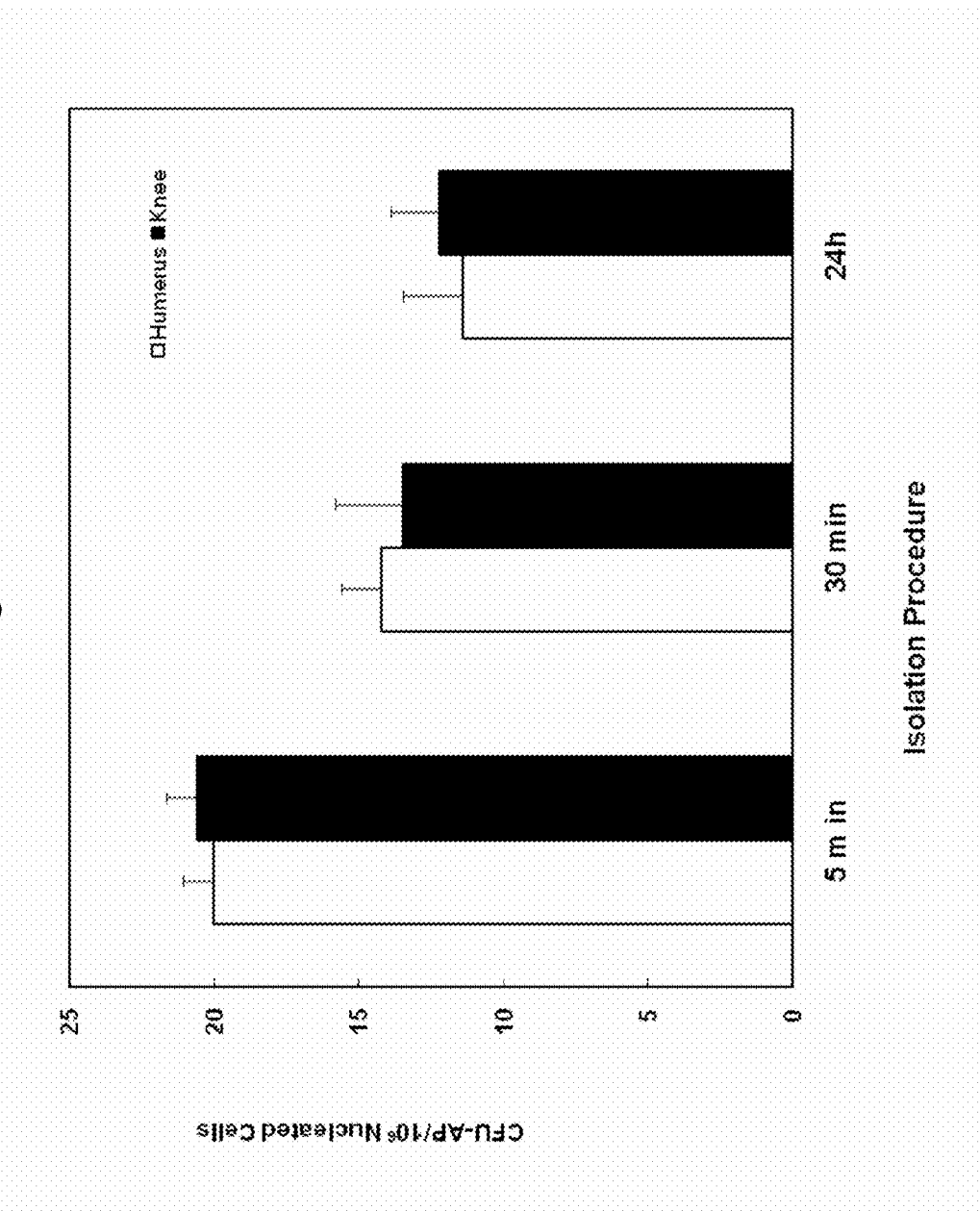

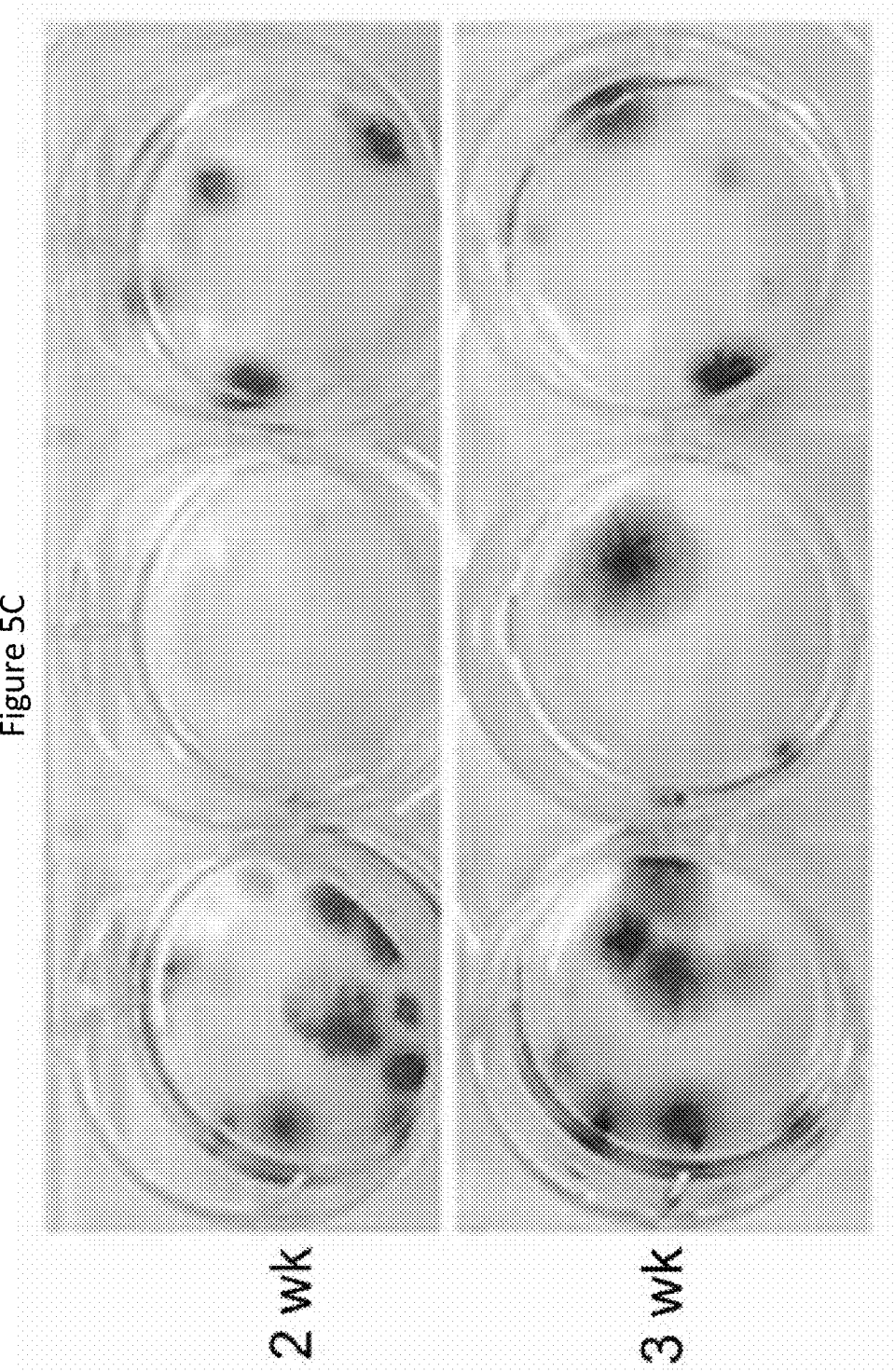

CONCENTRATION OF STEM CELLS OBTAINED DURING ORTHOPAEDIC SURGERIES

CROSS-REFERENCE TO RELATED APPLICATIONS

This application claims the benefit of U.S. Provisional Application No. 60/968,264, filed Aug. 27, 2007, the entire disclosure of which is incorporated by reference herein.

FIELD OF THE INVENTION

The present invention relates to the field of surgery and, more particularly, to the isolation and treatment of bone marrow aspirate obtained from arthroscopic and or open sites during reconstructive surgeries.

BACKGROUND OF THE INVENTION

Pluripotent or multipotent stem cells have been detected in multiple tissues in adult mammals, participating in normal replacement and repair while undergoing self-renewal. Bone Marrow Stromal Cells ("BMSCs" or "stromal cells") are pluripotent stem cells capable of differentiating into osteogenic, chondrogenic, adipogenic and other mesenchymal lineages in vitro. Because of their capacity to differentiate into at least three lineages (osteogenic, chondrogenic and adipogenic) when cultured under certain conditions, BMSCs have been used generally to treat osteogenesis imperfecta, tendon and ligament disruption at the joint, and wounds involving multiple phenotypic switches between fibrous, hyaline cartilage, fibro-cartilage, and bone.

Although BMSCs have been successfully isolated, these stem cells lack definite specificity because there is no known exceptional phenotypic marker. The isolation of bone marrow has been also a lengthy, time-consuming procedure and one that cannot be easily accomplished in the operating room. Isolation of BMSCs immediately during surgery can aid the surgeon and enhance the bone to tendon healing, eliminating the need for additional surgeries for the patient.

BRIEF SUMMARY OF THE INVENTION

The present invention provides compositions and methods for the reliable withdrawal of bone marrow aspirate and expeditious concentration of bone marrow stromal cells drawn from different surgical sites (for example, the proximal humeral head during rotator cuff repair, or the distal femur during ACL surgery) during arthroscopic surgery. These cells can be concentrated in a clinically fast manner (less than 10 minutes) for possible re-implantation during the same procedure. A bone marrow aspiration kit (Arthrex) was employed to expedite and simplify the harvesting of bone marrow from these sites.

Other features and advantages of the present invention will become apparent from the following description of the invention which refers to the accompanying drawings.

BRIEF DESCRIPTION OF THE DRAWINGS

FIG. 1B illustrates a step subsequent to that shown in FIG. 1A, wherein a "Buffy Coat" containing pluripotent cells is isolated.

FIG. 4A shows that a 5-minute centrifugation yields significantly more osteogenic progenitor cells than a 30 minute spin or bone marrow aspirate plated for 24 hours.

FIG. 5C shows increased positive colonies cultured from the 5 minute fractionation samples compared to the 30-minute centrifugation and 24 hour plated cells.

DETAILED DESCRIPTION OF THE INVENTION

Figure 1A:
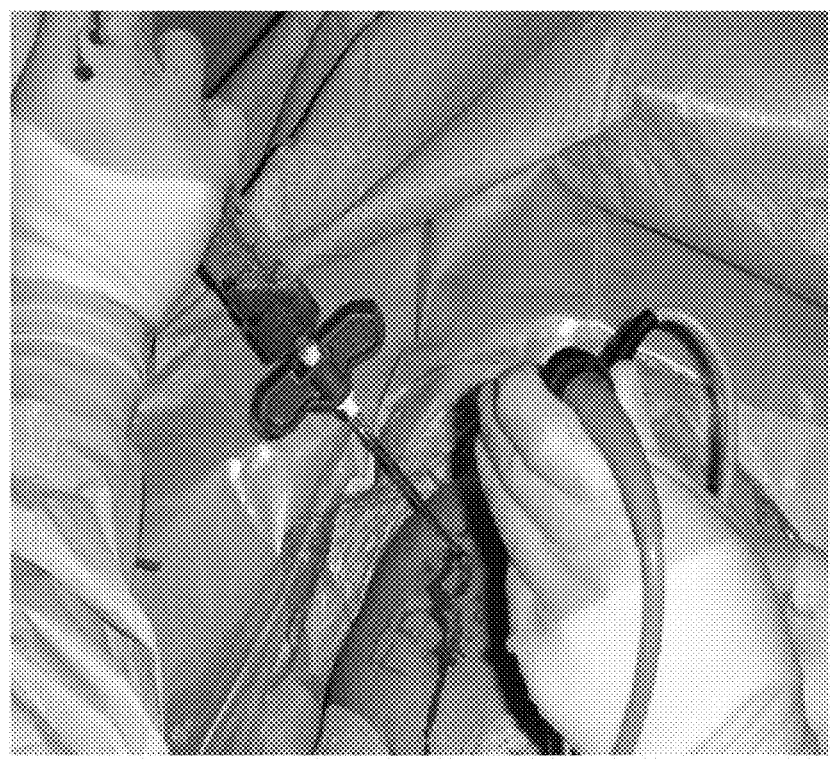
FIG. 1A illustrates an initial step during isolation of human bone marrow stromal cells from the proximal humerus, in accordance with an embodiment of the present invention.

The terms "mesenchymal stem cells" and "bone marrow stromal cells" refer to cells which are found within the bone marrow and exhibit multilineage differentiation capacity. Mesenchymal stem cells and stromal cells can be expanded ex vivo, and induced (either in vitro or in vivo) to terminally differentiate into osteoblasts, chondrocytes, adipocytes, tenocytes, myotubes, neural cells, and hematopoietic-supporting stroma.

The present invention also provides compositions including isolated BMSCs or mesenchymal cells, the compositions having osteogenic and/or osteoinductive cell proliferative activity. The BMSCs are concentrated during surgery by overlaying the bone marrow aspirate onto a sucrose gradient. Further extraction of the buffy coat provides a concentrated volume containing BMSCs.

The present invention is comprised of three steps during surgery: (i) concentrating bone marrow stromal cells from a bone marrow aspirate obtained from different surgical sites during routine orthopaedic (open or arthroscopic) procedures (ii) utilizing a short fractionation method (less than 10 minutes) to obtain the BMSCs and (iii) utilizing a sucrose gradient to concentrate the bone marrow stromal cells.

In a particular and exemplary only embodiment (described in more detail below), bone marrow aspirates are obtained from two different sites, the proximal humeral head (rotator cuff repair) and the distal femur (ACL tunnel surgery), and then rapidly isolated and compared. In the embodiments according to the present invention, autologous bone marrow aspirates are contemplated. In an autologous transplant, the individual to receive therapy donates his/her own stem cells. In this invention, the stem cells donated can be used for re-implantation during the same procedure. Harvesting of the bone marrow from the individual is typically performed using a 14 gauge needle. The bone marrow is a thick, red liquid and is preferably extracted by a syringe.

Obtaining Bone Marrow

Bone marrow aspirates (BMA) from the proximal humerus and distal femur were obtained from forty-two consented adult patients (21 patients/site) undergoing shoulder or knee surgery. Patients were screened and excluded from the study if they had a previous history of hepatitis, AIDS, steroid use and or chemotherapy. The age of the donors for bone marrow aspirates varied between 18 and 86 years with the mean age being 54.6+19 (Range: 18-86) years for surgeries pertaining to the proximal humerus and 43.1+13.7 (Range: 18-80) for the distal femur. Bone marrow aspirates were collected during routine rotator cuff or ACL surgeries as indicated for the original diagnosis with no alteration in the surgical approach or procedure. A 14 gauge aspiration needle (Arthrex Inc.) fit with a 60 cc syringe containing 1000 U of preservative free sodium heparin in 1.0 ml of saline solution was used for all surgeries. The first anchor site, in a rotator cuff repair, has a small tap which is used to make a reproducible tunnel for suture anchor placement. The needle was inserted 25 mm into the tunnel and bone marrow was reliably and reproducibly aspirated over a minute time interval. The anchor was placed in the tunnel after withdrawal of the needle. For ACL surgery, the 14 gauge aspiration needle was placed into a previously positioned femoral tunnel and inserted into the lateral intramedullary canal for bone marrow aspiration.

The gradient for the isolation of BMSC was prepared by adding 15 cc of a 17.5% sucrose solution into a 50 cc polystyrene conical centrifugation tube. 10 cc of freshly isolated bone marrow was gently overlaid onto the sucrose gradient using the same 14 gauge aspiration needle used during surgery to obtain the bone marrow aspirate. Tubes were centrifuged at 1500 rpm (201 g) for 5 minutes to obtain the buffy coat. The buffy coat (approximately 5-7 cc) containing concentrated BMSC was drawn up into a 60 cc syringe fitted with the aforementioned 14 gauge aspiration needle.

Comparison of BMSC Concentration Procedures

The most commonly used method for progenitor cell isolation from whole marrow aspirates consists of a 30 minute centrifugation @ 1500 rpm in a ficoll or histopaque gradient. In order to adequately test the rapid isolation (5 minutes centrifuge spin) procedure, bone marrow aspirates were passed through a 70 micron filter and divided into three equal volumes. BMSC were isolated according to three different procedures. (1) isolation utilizing a histopaque gradient and 30 min. of centrifugation at 1500 rpm (201 g) followed by extraction of the buffy coat; (2) isolation involving plating the bone marrow cell aspirate for 24 h., and aspiration of non-adherent cells at this time; and (3) immediate isolation utilizing a 17.5% sucrose gradient and 5 min. of centrifugation at 1500 rpm followed by buffy coat extraction. The immediate isolation method (3) is preferred, as cell isolation resulted in a significant increase in the amount of BMSCs that were isolated in comparison to the other methods.

Culture Conditions and Viability of Bone Marrow Stromal Cells

For each sample, prior to plating, the total number of nucleated cells per 1.0 ml of bone marrow aspirate was counted and recorded using a Coulter Counter and cell viability was assessed by trypan-blue exclusion using a hemocytometer. The buffy coat from isolations 1 and 2 were immediately resuspended in a standard stem cell media containing α-MEM phenol red free, 10% fetal bovine serum (FBS), 0.1% penicillin, 50||g/ml ascorbic acid, and $10^{-8}$ M dexamethasone. For isolation 2, media was aspirated, to remove non-adherent cells after 24 h of incubation, and replaced with fresh media as stated above. For all experiments, cells were plated into two 6-well Falcon dishes/patient at a concentration of $1.0\times10^{-6}$ cells/9.6 cm2, incubated at 370 C, in 5% $CO_2$, for 7, 14 or 21 days to promote expression of an osteoblast phenotype. Cells were fed 2 times per week.

Quantification of Progenitor Cells

For quantification of progenitor cells, alkaline phosphatase positive cells were quantified on day 7. Alkaline Phosphatase positive cells were counted to assess the number of osteogenic progenitor cells present. Eight or more cells in a cluster were defined as colony-forming units (CFU) and those staining positive for alkaline phosphatase were defined as Colony-Forming Units-AP (CFU-AP). After fixing, the cells were incubated for 30 minutes in 0.2 M Tris Buffer, pH 8.3 with AS-MX phosphate as a substrate and Fast Blue as a stain. The ALP positive cells, stained blue/purple and osteogenic progenitor cell concentration and prevalence were calculated with respect to nucleated cells and volume of bone marrow aspirated. Data was then analyzed according to site.

FIG. 1A illustrates an initial step during the immediate isolation of human bone marrow stromal cells (bone marrow aspirate) from proximal humerus 10 during orthopaedic surgery. FIG. 1B illustrates a step subsequent to that shown in FIG. 1A, i.e., about 5 min. isolation of "Buffy Coat" 50 containing pluripotent stem cells.

Light Microscopy Showing BMSC's in Culture

Figure 2A:
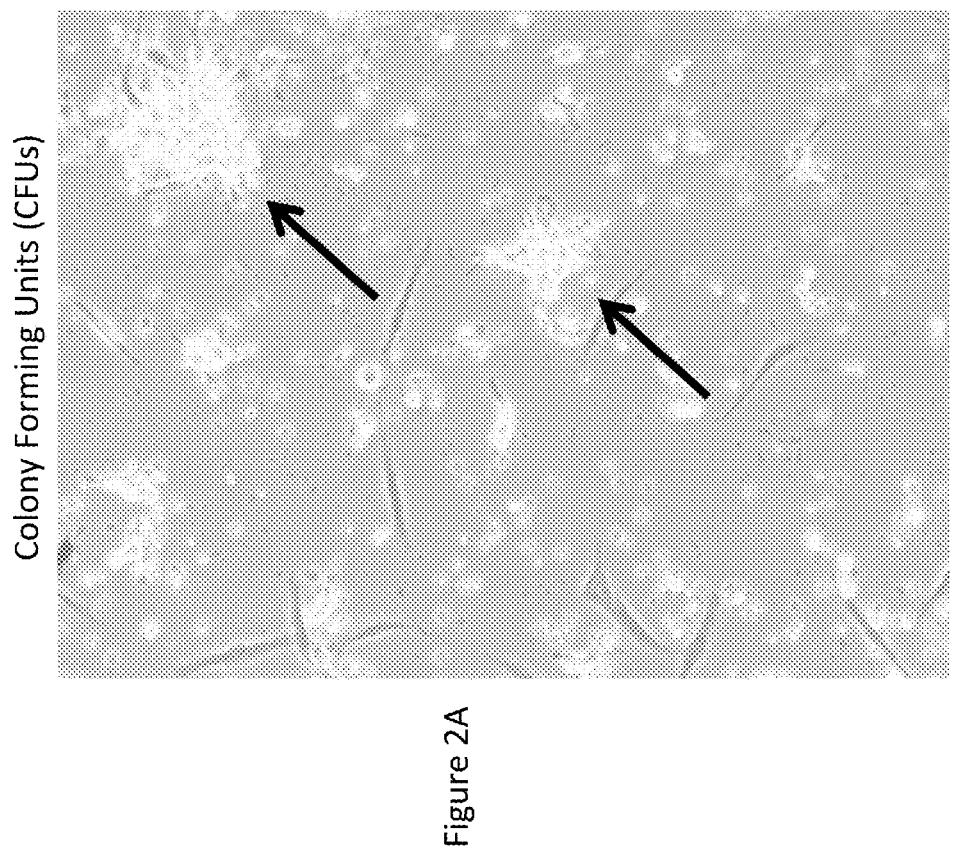
FIG. 2A illustrates BMSCs in culture under light microscopy, wherein Colony Forming Units (indicated by arrows) are shown after 48 h in culture.
Figure 2B:
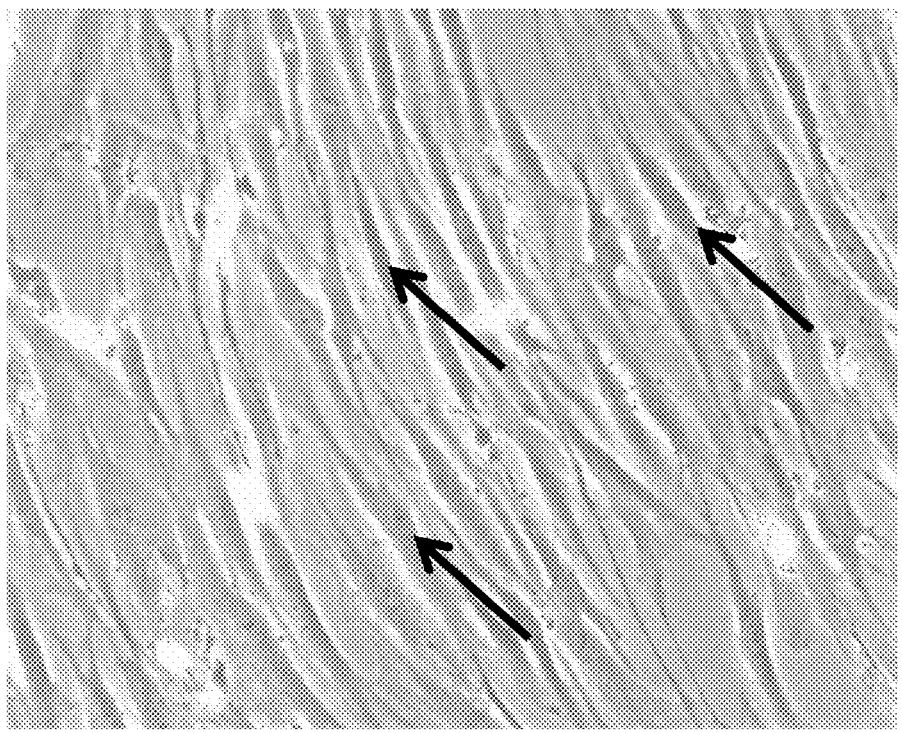
FIG. 2B shows bone marrow stromal cells after 7 days in culture, wherein BMSCs tend to align together (arrows) in a well-organized, parallel fashion.

FIG. 2A illustrates BMSCs in culture under light microscopy, wherein Colony Forming Units (CFUs indicated by arrows) are shown after about 48 h in culture. FIG. 2B shows bone marrow stromal cells after 7 days in culture. As shown in FIG. 2B, BMSCs tend to align together (see arrows) in a well-organized, parallel fashion.

Figure 3A:
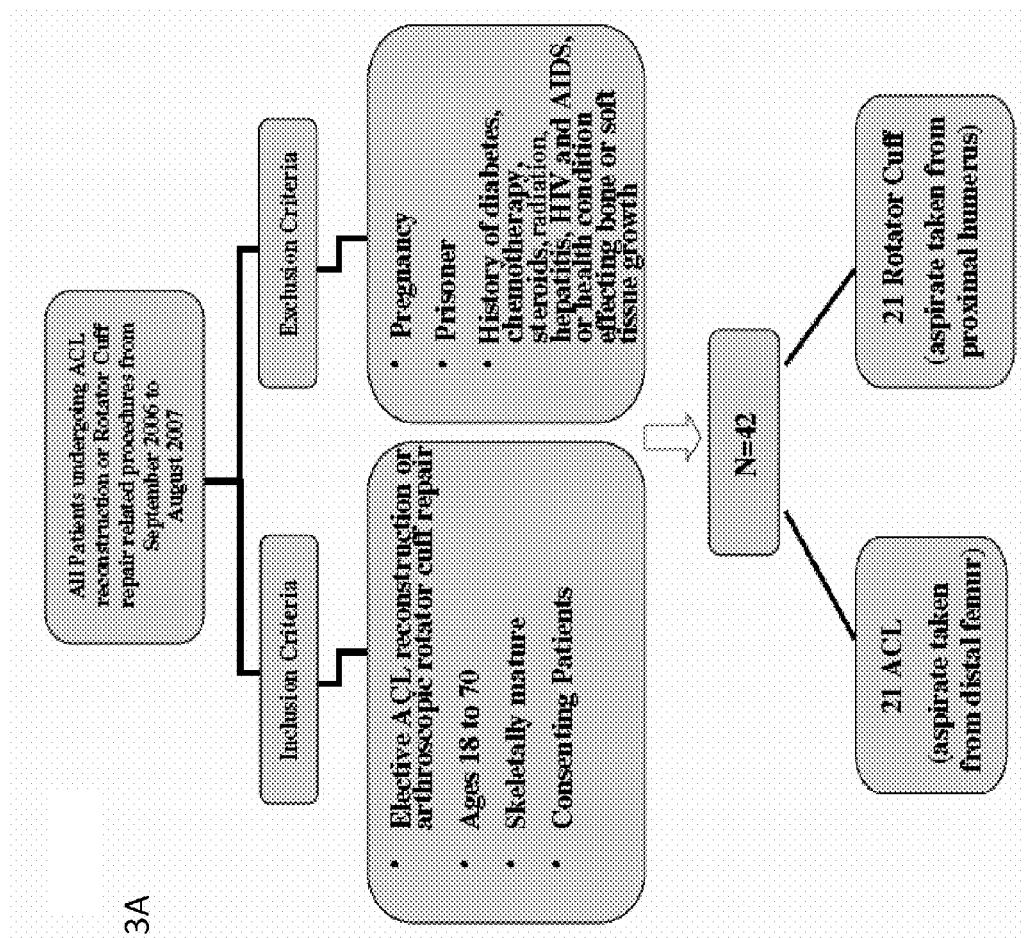
FIG. 3A shows inclusion and exclusion criteria

FIG. 3A shows how patients undergoing anterior cruciate ligament (ACL) reconstruction or rotator cuff repair were selected. Inclusion criteria and exclusion criteria are indicated. 42 patients were enrolled and bone marrow was harvested from the femurs of 21 patients undergoing ACL surgery and from the humeri of 21 rotator cuff surgery patients.

The table below summarizes BMSC aspirates harvested from consented patients (forty-two adults) undergoing surgery. Aspirates were obtained from two sites, the proximal humeral head (during rotator cuff repair) and the distal femur (during ACL tunnel surgery):

|  | Knee | Shoulder |
| --- | --- | --- |
| Number of Aspirates | 21 | 21 |
| Gender | 5 Female | 6 Females |
|  | 16 Male | 15 Males |
| Average Age | 43.1 ± 13.7 | 54.6 ± 19 |
| Average Volume of Aspirate (cc): | 27.3 ± 10.7 | 19.5 ± 8.4 |

Figure 3B:
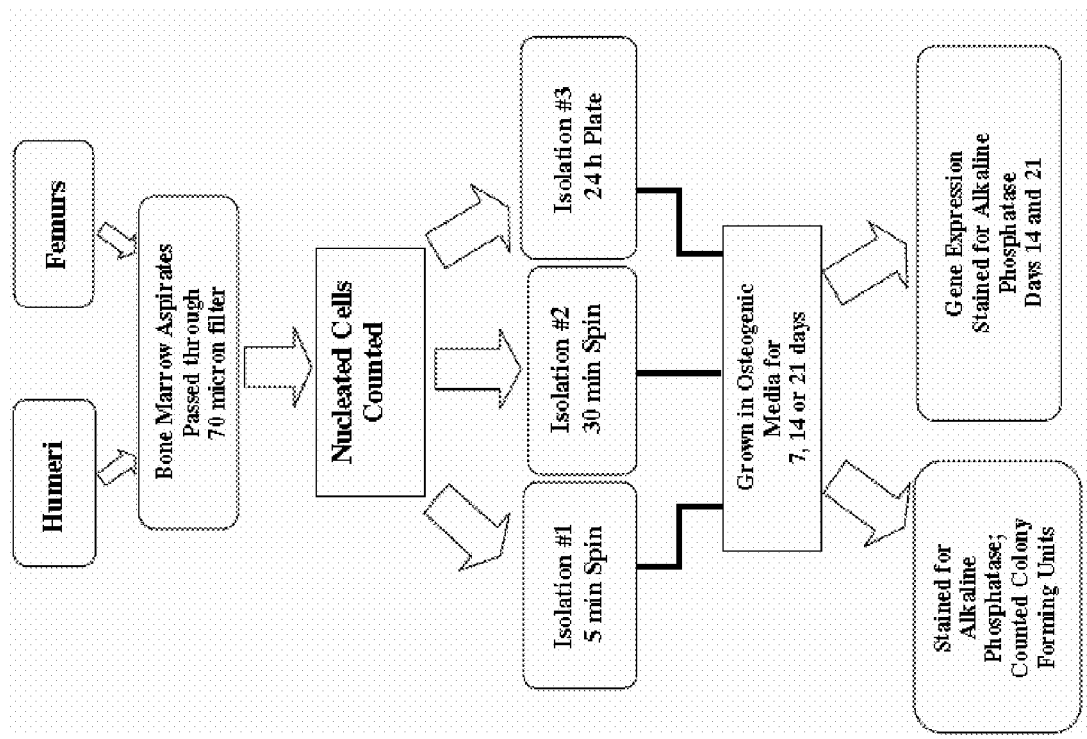
FIG. 3B shows the experimental outline where marrow was collected from either humeri or femurs.
Figure 4B:
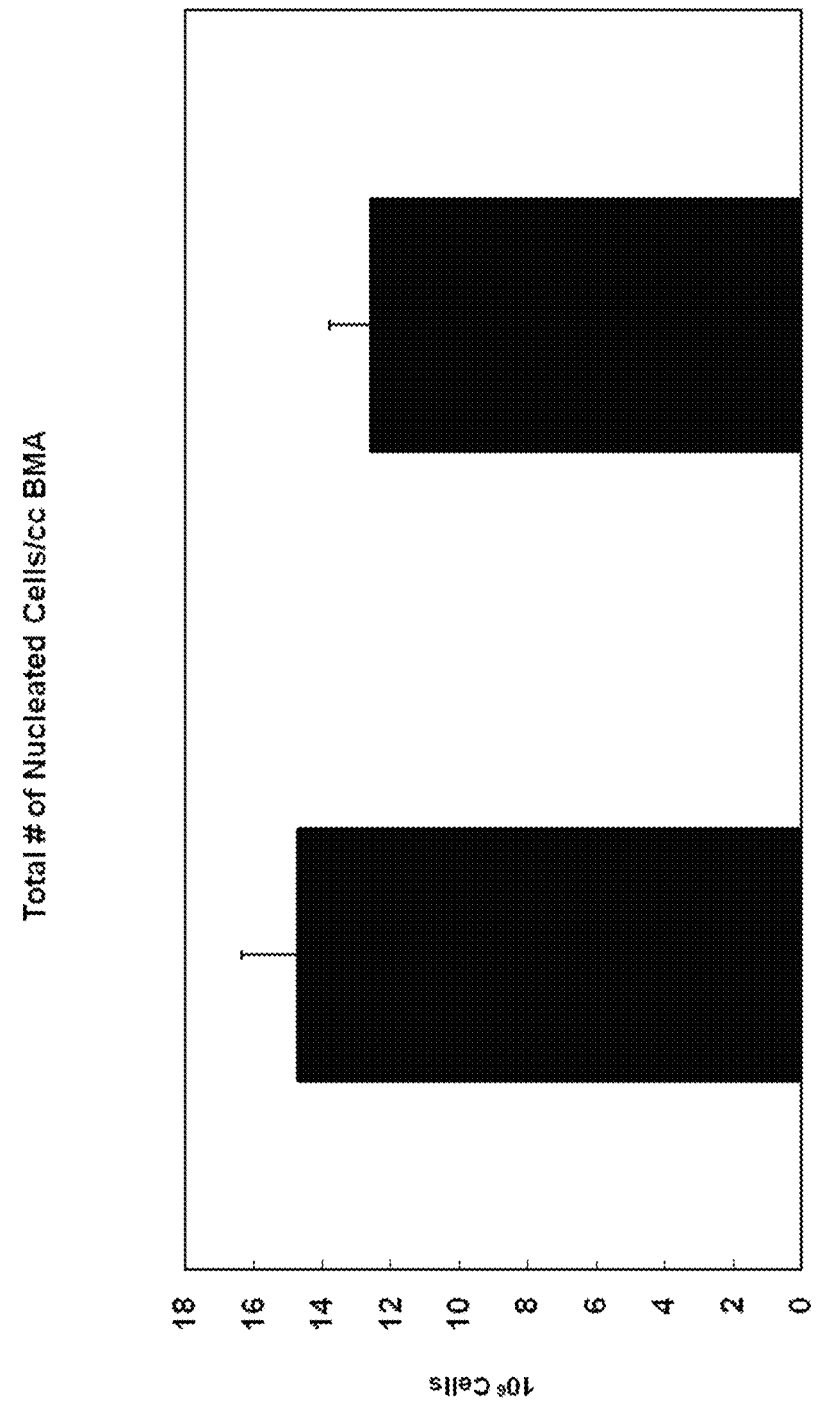
FIG. 4B illustrates the nucleated cell count (total number of Nucleated Cells/cc of BMA) found in 1 cc of bone marrow aspirate.

FIG. 3B shows the experimental outline where marrow was collected from either humeri or femurs and was filtered to exclude blood clots. The buffy coat was then isolated after either a 5-minute fractionation (Isolation #1), a 30-minute fractionation (Isolation #2) or after plating and culturing the adherent mesenchymal cells for 24 hours (Isolation #3). Cells from each isolation were then plated and grown in media for 7, 14 and 21 days FIG. 4A shows that a 5-minute (5 min) centrifugation yields significantly more osteogenic progenitor cells than a 30 minute (30 min) spin or bone marrow aspirate plated for 24 hours (24 hr). Comparisons were made between isolation conditions for humeri (Humerus) or femurs (Femur) alone FIG. 4B illustrates the nucleated cell count (total of Nucleated Cells/cc of BMA) present in 1 cc of bone marrow aspirate. The total number of nucleated cells per 1.0 cc of aspirated marrow was consistently higher in the proximal humerus as compared with the distal femur, but the differences are not significant. A mean of about $15.35\times10^6$ nucleated cells were contained in each 1.0 cc of proximal humerus aspirated compared to about $14.5\times10^6$ for the distal femur.

Figure 4C:
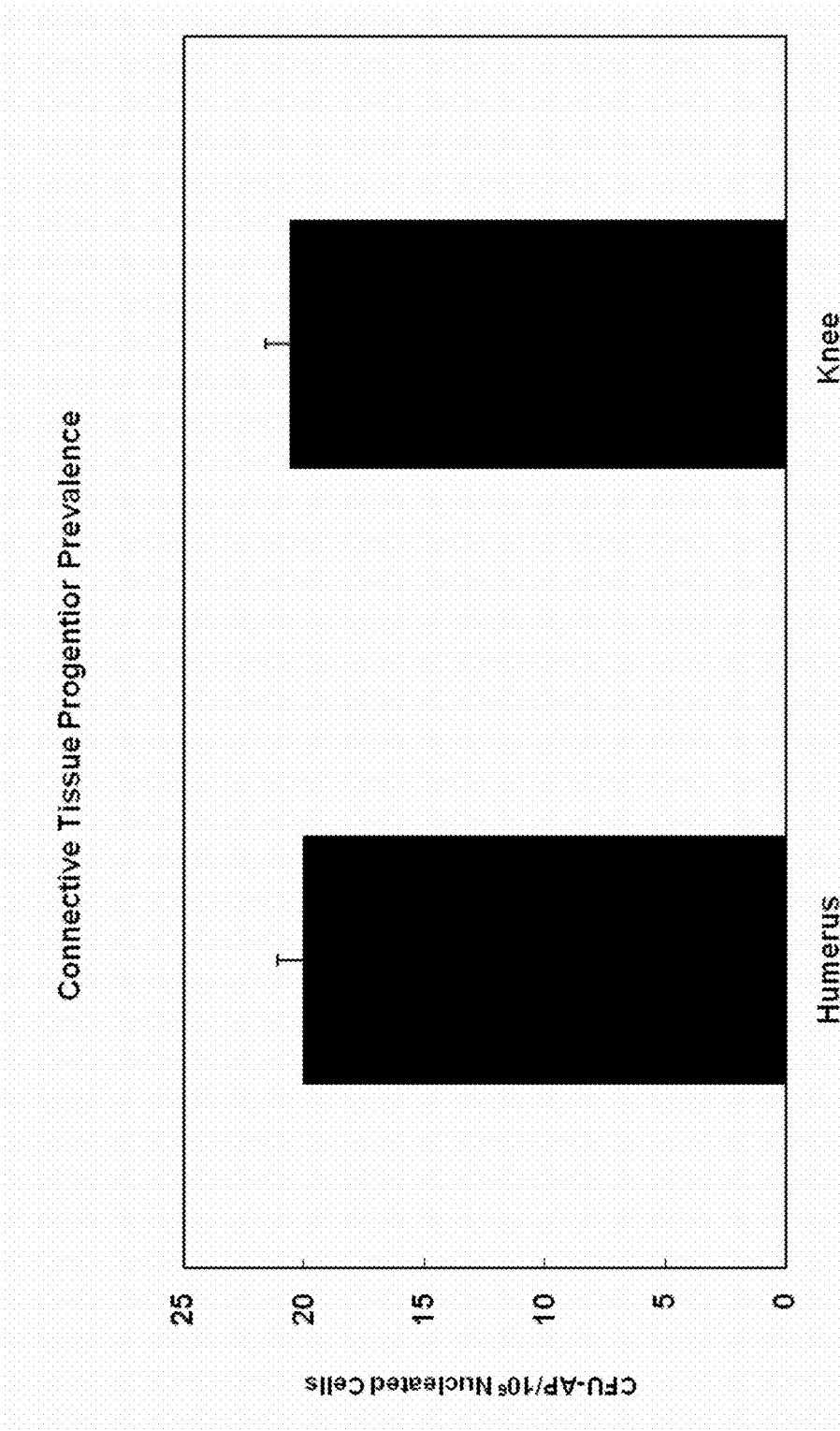
FIG. 4C shows the prevalence of connective tissue progenitor cells (CTP prevalence) found in 1 million nucleated cells.

FIG. 4C shows the prevalence of connective tissue progenitor cells (CTP prevalence). A mean 19.9 connective-tissue progenitor cells (CFU-AP/$10^6$ nucleated cells) were identified per one million nucleated cells aspirated from the proximal humerus. This value is about similar to the measured 19.8 connective-tissue progenitor cells in the distal femur.

Figure 5A:
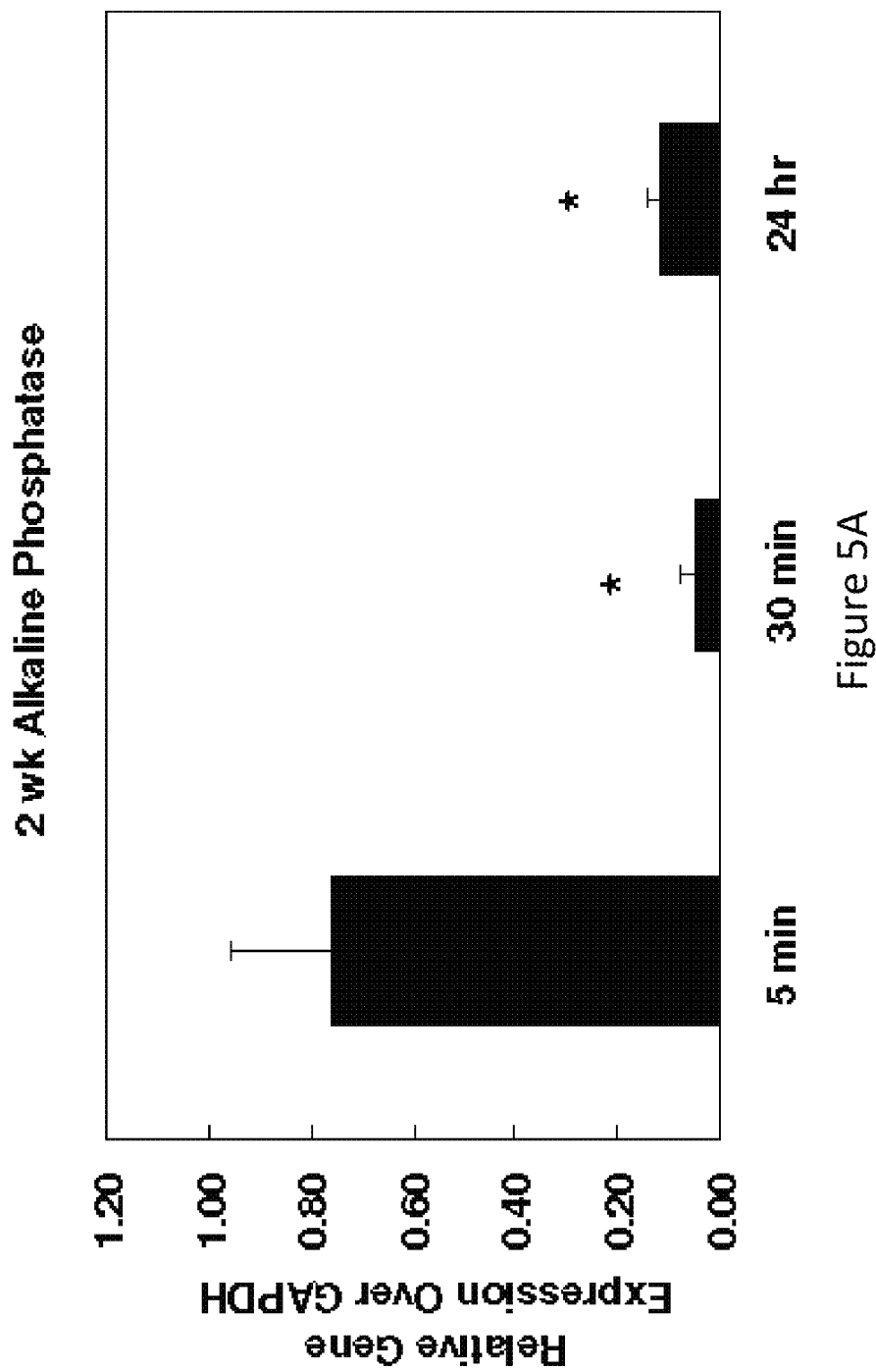
FIG. 5A shows that after three weeks in culture, alkaline phosphatase transcripts in the 5 minute fractionated samples were still significantly higher than the 30-minute and 24 hour samples.
Figure 5B:
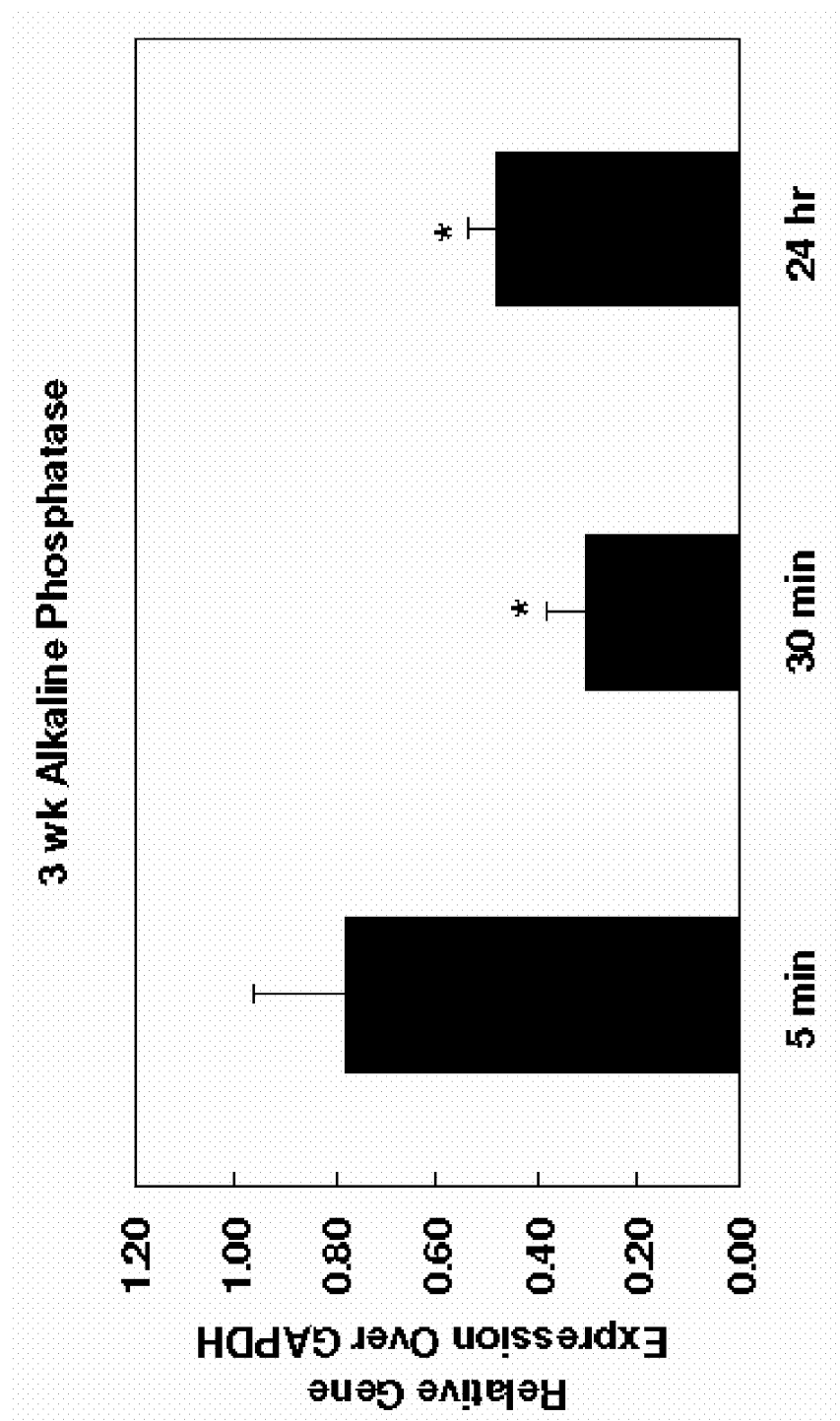
FIG. 5B shows alkaline phosphatase staining at 2 and 3 weeks.

FIG. 5 shows that a 5-minute (5 min) fractionation gives a significantly higher expression of alkaline phosphatase mRNA levels compared to the 30-minute (30 min) fractionated samples and the 24 hour (24 hr) plated marrow after two weeks in culture (15.6 fold and 7.8 fold respectively) (5A). After three weeks in culture, alkaline phosphatase transcripts in the 5 minute fractionated samples were still significantly higher than the 30-minute and 24 hour samples three fold and two fold respectively (5B). Alkaline phosphatase staining at 2 weeks (2 wk) and 3 weeks (3 wk) shows increased positive colonies cultured from the 5 minute fractionation samples compared to the 30-minute centrifugation and 24 hour plated cells (5C). However, cells harvested from the 30-minute fractionation exhibited less alkaline phosphatase staining than the cells adhering for 24 hours.

The results of the experiments outlined above demonstrate that immediate isolation of BMSC at the time of surgery results in significantly more cells than the cells obtained according to known prior-art isolation procedures. The results above also demonstrate that the proximal humerus and the distal femur are suitable sites for harvesting bone marrow aspirates and are comparable to aspirates taken from the iliac crest, thus offering to surgeons additional opportunities for further enhancement of the bone to tendon healing during surgical procedures. Bone marrow aspirates are fast and easily obtained, and purified to pluripotent cells in an efficient manner from surgical sites, as seen in this invention.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of conducting arthroscopic surgery, the method consisting of the steps of:
    harvesting a bone marrow aspirate from proximal humeral head or from distal femur undergoing arthroscopic or open orthopedic surgery;
    subjecting, during the arthroscopic or open orthopedic surgery, the bone marrow aspirate to a centrifugation process for 5 minutes to obtain concentrated multipotent cells of the bone marrow aspirate and a residual component;
    separating the concentrated multipotent cells from the residual component; and
    re-implanting, during the same arthroscopic or open orthopedic surgery, the concentrated and separated multipotent cells into the proximal humeral head or the distal femur, or to the proximal humeral head or the distal femur, to promote tissue growth.

2. The method of claim 1, wherein the arthroscopic or open orthopedic surgery is rotator cuff repair or ACL repair.

* * * * *